United States Patent [19]

Klein

[11] Patent Number: 4,486,405
[45] Date of Patent: Dec. 4, 1984

[54] PIGMENTED COSMETIC VEHICLE CONTAINING A MIXTURE OF ALKOXYLATED SURFACTANTS

[75] Inventor: Robert W. Klein, Fort Washington, Pa.

[73] Assignee: William H. Rorer, Inc., Fort Washington, Pa.

[21] Appl. No.: 486,382

[22] Filed: Apr. 19, 1983

[51] Int. Cl.³ ...................... A61K 7/42; A61K 7/021; A61K 47/00; C04B 31/40
[52] U.S. Cl. ........................................ 424/59; 424/60; 424/63; 424/358; 106/308 F
[58] Field of Search ...................... 424/63, 59, 60, 358; 252/174.22, 174.25; 106/3, 288 R, 308 F

[56] References Cited
U.S. PATENT DOCUMENTS
3,751,562  8/1973  Nichols ........................... 424/358 X
4,145,413  3/1979  Usdin et al. ........................... 424/63

FOREIGN PATENT DOCUMENTS
2418066  11/1975  Fed. Rep. of Germany ... 106/308 F
50-42054   4/1975  Japan ...................................... 424/63
1421713    1/1976  United Kingdom .

OTHER PUBLICATIONS
Chem. Abs., 88:126187b=Japanese Kokai 78, 06,434.

Primary Examiner—Esther M. Kepplinger
Assistant Examiner—Shawn P. Foley
Attorney, Agent, or Firm—James A. Nicholson; Alexis Barron; Martin F. Savitzky

[57] ABSTRACT

A spreadable, flowable and greaseless cosmetic coverup composition which includes a relatively large amount of pigment and a mixture of two alkoxylated surfactants.

15 Claims, No Drawings

PIGMENTED COSMETIC VEHICLE CONTAINING A MIXTURE OF ALKOXYLATED SURFACTANTS

FIELD OF THE INVENTION

This invention relates to pigmented cosmetic compositions.

Cosmetic compositions are compositions which are applied to the body, usually to the skin, hair, nails or teeth, and are either liquid or solid preparations comprising a cosmetic material and a carrier. The term "cosmetic material" is used herein broadly to include materials which impart aesthetic and/or other functional properties to the composition. To be cosmetically acceptable, both the cosmetic material and the carrier must be non-toxic, non-irritating and inoffensive.

The carrier permits the cosmetic material to be easily applied to the body and may be either water, an organic liquid or solid, an inorganic liquid or solid, or mixtures thereof. Free-flowing liquid carriers may comprise water, alcohol, oils or combinations thereof.

Although some cosmetic applications may utilize a multiphase composition when purportedly derives benefit from the separation of its ingredients, for most applications, including facial cosmetics, it is cosmetically desirable that the cosmetic material be evenly distributed throughout the carrier. A further requirement of a cosmetically acceptable composition is that the cosmetic material not only be evenly dispersed throughout the carrier, but that the composition be capable of easy and uniform application. One means of achieving these goals, if the desired cosmetic material is not soluble in the chosen carrier, is the use of a dispersing or suspending agent. Limited quantities of insoluble material can be evenly distributed or emulsified throughout a carrier and produce an easily applicable composition using one or more dispersing or suspending agent.

Many cosmetic compositions, including the facial cosmetics, are used as means to impart color to the skin and include one or more pigments as the coloring agent. This invention relates to cosmetic compositions which include a relatively large amount of one or more pigments.

REPORTED DEVELOPMENTS

Dispersing or suspending agents have been used in the prior art to evenly distribute small amounts of pigment, on the order of less than 1% to about 15%, in various media. See, for example, U.S. Pat. Nos. 2,175,213 (dispersing small amounts of pigments together with metal flakes in a vanishing cream base resulting in a salve); 4,362,715 (an alcohol gel incorporating about 13 percent pigment and propoxylated ethoxylated cetyl alcohol as the surfactant).

It is often desirable to achieve a heavy skin coverup using a pigmented composition in order to either conceal a serious permanent blemish, such as a port wine stain, or to protect exposed photo-sensitive skin and post-skin cancer treated skin. However, the incorporation of relatively large amounts of pigment in a cosmetic composition results in a highly viscous, now-flowing unctuous or usually greasy compositions. The addition of dispersing and suspending agents to these products will often increase their flow, but they apply to the skin in a streaking, non-uniform pattern. Additionally, upon drying, these compositions feel unacceptably unctuous. Compositions which are currently in the marketplace and that are specifically formulated to permit the application of large amounts of pigment comprise two component systems consisting of highly pigmented unctuous, heavy creams that cannot be spread over the skin. These creams are slowly patted on the skin, followed by dusting lightly pigmented dry powders over this first layer. An example of such a two-component vehicle is commercially marketed under the trademark "Covermark".

The present invention relates to a cosmetically elegant aqueous pigmented cosmetic vehicle comprising one uniform component and two to four times the total pigment concentrations disclosed in the prior art pigmented cosmetics.

SUMMARY OF THE INVENTION

The present invention relates to an aqueous pigmented cosmetic composition which can be prepared in a greaseless, flowable, spreadable, and non-streaking form and which comprises:

about 23 to about 62 weight percent of pigment.

More specifically, compositions within the scope of the present invention comprise:

about 23 to about 62 weight percent of pigment;

about 0.5 to about 6.5 wt percent of a first alkoxylated surfactant;

about 0.5 to about 6.5 wt percent of a second alkoxylated surfactant;

about 30 to about 70 wt percent of $H_2O$;

wherein the total amount of surfactant is about 2 to about 11.5 percent of the total weight of the composition, and about 8.5 to about 19 percent of the pigment weight.

DETAILED DESCRIPTION

The term "pigments" as used herein means both primary pigments that act to form either an opaque white or colored cover when applied to the skin, as well as secondary pigments that extend the covering power of the primary pigments. Primary pigments include, for example, titanium dioxide, zinc oxide, kaolin, titanium dioxide-mica, iron oxides and the like. Secondary pigments include, for example, talcum, calcium carbonate, silica powder and the like.

In general, the amount of primary pigment comprising the composition will be at least about 14.5 percent of the total weight of the composition. A preferred composition includes from about 30 percent to about 60 percent by weight of pigment in the cosmetic composition.

Various additives may be incorporated in the cosmetic composition, for example, to preserve the aqueous systems, to fragrance them and to alter the cosmetic qualities. Gums, polymers, or both may be added to aid in suspending solids, to act as film formers or contribute towards a waterproof coverup of the skin. Humectants and emollients may be included to improve the feel of the skin. Ultraviolet absorbers, antibiotics, bactericides, fungicides, disinfectants, dyes, pearlescents, insect repellants, water repellants, keratolytic agents, absorbents, and anti-caking agents may also be included. For a list of commercially available ingredients, see McCutcheon's 1982 *Functional Materials*.

In the presence of some combination of additives that are both water soluble and water insoluble materials, for example, oils, fats and waxes, certain ratios of the alkoxylated surfactants included in the present invention may act as emulsifiers, forming stable lotion and cream vehicles. Accordingly, the term "surfactant", as used herein, includes materials which may be described as surfactants, wetting agents, detergents, or emulsifiers.

According to the present invention, two different classes of alkoxylated surfactant must be employed in the cosmetic composition. The term "class" as used herein is employed in McCutcheon's *Emulsifiers and Detergents,* pages 294–299 (McCutcheon Publishing Co., 1982), herein incorporated by reference. Examples of some different "classes" of alkoxylated surfactants are: those derived and based upon lanolin; those derived and based upon sorbitan; carboxylated alcohol ethoxylates; ethoxylated alcohols; ethoxylated alkyl phenols; ethoxylated amines or amides; ethoxylated fatty acids; ethoxylated fatty esters and oils; propoxylated and ethoxylated fatty acids, alcohols or alkyl phenols; sulfates and sulfonates of ethoxylated alkyl phenols; sulfates of ethoxylated alcohols; and, block polymers of ethylene and propylene oxide.

Certain of these alkoxylated nonionic surfactants may be modified to exhibit some anionic properties (cryptoanionic) and can be utilized for one, but not both, of the two different surfactant classes. Examples of acceptable modified ethoxylates are phosphated ethoxylated fatty amines and salts thereof (such as Jorphox ™, Jordan Chemical Co.) and pareth-25-7 carboxylic acid and salts thereof (Surfine ™, Finetex Inc.).

The alkoxylated surfactants utilized in the present invention comprise polyethoxylated, polypropoxylated or polyethoxy-polypropoxy copolymer surfactants wherein the ethylene oxide average for any given polyethoxy or polypropoxy-polyethoxy copolymer chain within a molecule or polymer block is between 3 and 40 monomer units on the average.

A preferred pigmented aqueous cosmetic composition according to this invention includes the amounts of pigment and said surfactants as described above, wherein:

said first alkoxylated surfactant is a polyethoxylated ether of a fatty acid alcohol, a polyethoxylated ether derivative of lanolin or partial fatty acid esters thereof, a polyethoxylated derivative of sorbitol or partial fatty acid ester thereof, or a polyethoxylated derivative of glycerol or partial fatty acid ester thereof; and said second alkoxylated surfactant is a polyethoxylated fatty acid ester, a polypropoxy/polyethoxy copolymer, an acetylated derivative of said first alkoxylated surfactant, or a phosphated polyethoxylated fatty acid amine oxide or salt thereof.

As used herein, the terms "fatty acid", "fatty", "mixture of fatty acids" or chemical derivatives thereof mean the mixture of organic carboxylic acids or derivatives thereof derived from a naturally occurring oil or fat or a hydrogenated product thereof including coconut oil, castor oil, palm kernel oil, cottonseed oil, peanut oil, olive oil, palm oil, sunflower seed oil, sesame oil, corn oil, safflower oil, poppyseed oil, teaseed oil, kapok oil, rice bran oil, grain sorghum oil, rapeseed oil, linseed oil, soybean oil, perilla oil, hempseed oil, wheatgerm oil, rubberseed oil, tung oil, oiticica oil, cacahuanache oil, whale oil, pilchard oil, Japanese sardine oil, menhaden oil, herring oil, fish liver oil, tallow, milk fat or lard.

Exemplary surfactants that can be included in the cosmetic composition of the present invention are represented by Formula I below

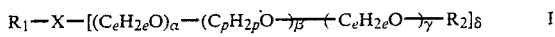

wherein:

$R_1$ is H, an alkyl or alkenyl radical derived from a fatty acid or mixture of fatty acids, a glyceryl, lanolin, or a sorbital radical derived from the removal of one hydroxyl group thereof, a fatty acid ester derivative of a glyceryl, lanolin, or sorbital radical derived from the removal of one hydroxyl group thereof, respectively, an alkyl phenyl radical or $R_3$;

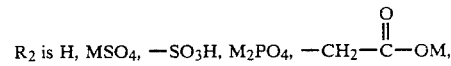

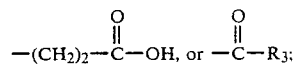

$R_3$ is a straight chain alkyl group having about 1 to about 22 carbon atoms;

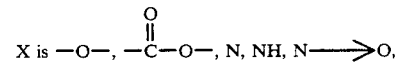

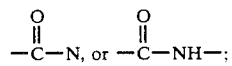

M is H or an alkali metal or ammonium cation;
e is 2 or 3;
p is 2 or 3;
e is not equal to p;
$\alpha$ is 1 to 40;
$\beta$ is 0 to 40;
$\gamma$ is 0 to 40;
$\delta$ is 1 or 2;
provided that if $\delta$ is 1, then $\alpha$ is 3 to 40;
provided that when X is N, N→O or

then $\delta$ is Z and $\alpha$ is 1 to 40;
further provided that if $R_2$ is MSO$_4$, SO$_3$H,

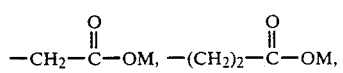

or M$_2$PO$_4$ for said first surfactant, then $R_2$ is H or

for said second surfactant;
further provided that if $\beta$ is greater than zero for said first surfactant, then $\beta$ and $\gamma$ are both equal to zero for said second surfactant;
further provided that if $\beta$ is not zero for both surfactants, then at least one of X or $R_1$ is different for said first and said second surfactants.

Preferred mixtures of surfactants are listed below:

(A) PEG Fatty Acid Ether and PEG/PPG Copolymer—a polyethoxylated fatty acid alcohol ether within Formula I in which:
 e is 2;
 $\beta$ and $\gamma$ are 0;
 X is 0;
 $R_1$ is an alkyl or alkenyl radical derived from a fatty acid; and
a polypropoxylated/polyethoxylated copolymer within Formula I in which:
 $\beta$ is greater than zero;
 X is 0;
 $R_1$ and $R_2$ are H.

(B) PEG Lanolin Derivative and PEG Glycerol Derivative—a polyethoxylated lanolin alcohol described by Formula I, where:
 e is 2;
 $\beta$ and $\gamma$ are 0;
 $\delta$ is 1;
 $R_1X$ is lanolin alkoxy;
and a polyethoxylated glycerol or partial fatty acid ester thereof described by Formula I, where:
 n is 2;
 $\beta$ and $\gamma$ are 0;
 $\delta$ is 1;
 $R_1X$ is glycerol or a partial fatty acid ester derivative of glycerol;
 provided that if $R_2$ is $MSO_4$ or $M_2PO_4$ for either of said first surfactants, then $R_2$ is H, $-SO_3H$, or

for the other of said surfactant.

(C) PEG Glycerol Derivative and PEG Fatty Acid Ester or Oil—a polyethoxylated glycerol or partial fatty acid ester of glycerol described according to Formula I, where:
 e is 2;
 $\beta$ and $\gamma$ are 0;
 X is 0;
 $\delta$ is 1;
 $R_1$ is a glyceryl radical or a fatty acid ester derivative of a glyceryl radical; and
a polyethoxylated naturally occurring oil, such as castor oil, described according to Formula I, where:
 e is 2;
 $\beta$ and $\gamma$ are 0;
 $R_1X$ is a fatty acid carboxy or a mixture of fatty acid carboxys, a fatty acid alkoxy or a mixture of fatty acid alkoxys, or a mixture of or acid carboxy and fatty acid alkoxys;
 $R_2$ is H.

(D) Anionic PEG Fatty Amide or Amine and PEG Sorbitol Derivative—an anionically modified N,N-bis polyethoxylated derivative of a fatty amine, a fatty amide, or mixtures of fatty amines or amides derives from a naturally occurring oil or fat, described by Formula I, where:
 e is 2;
 $\beta$ and $\gamma$ are 0;
 $\delta$ is 2;
 $\alpha$ is 1 to 40;
 X is N, N→O or

$R_1$ is one or more alkyl or alkenyl radicals derived from a fatty acid or a mixture of fatty acids;
 $R_2$ is $MSO_4$ or $M_2PO_4$;
and a polyethoxylated sorbitol or partial ester thereof described by Formula I, where:
 e is 2;
 $\beta$ and $\gamma$ are 0;
 $\delta$ is 1;
 $R_1X$ is sorbitol or a partial fatty acid ester of sorbital;
 $R_2$ is H or

Another preferred combination of surfactants according to this invention is described in which said first surfactant is of the formula

wherein:
 $\alpha$ is 3 to 40;
 $R_1X$ is lanolin alkoxy;
 $R_2$ is H, $MSO_4$, $M_2PO_4$, $SO_3H$ or

and in which:
 said second surfactant is of the formula

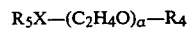

wherein:
 $\alpha$ is 3 to 40;
 $R_1X$ is sorbitol or a partial fatty acid ester derivative of sorbitol;
 $R_4$ is H, $MSO_4$, $M_2PO_4$, $SO_3H$ or

$R_3$ is a straight chain alkyl group having about 1 to about 22 carbon atoms;
 provided that if $R_2$ is $MSO_4$ or $M_2PO_4$, then $R_4$ is H or

EXAMPLES

The following examples are illustrative of the present invention.

EXAMPLE I

[48% pigments by weight]

| | |
|---|---|
| (A) water, deionized | 46.0 |
| polyoxyethylene (10) oleyl ether | 2.2 |

|   |   |   |
|---|---|---|
|  | poloxamer 124 | 3.8 |
| (B) | titanium dioxide | 20.0 |
|  | zinc oxide | 12.0 |
|  | talcum | 12.0 |
|  | iron oxides powder, brown | 4.0 |

Procedure: Blend and mix (A) for 1 minute. Blend and mix (B) for 2 minutes. Mix (A) rapidly to create moderate vortex and slowly add (B). Mix rapidly to form a uniformly thick liquid.

EXAMPLE IA

Repeating Example I, but with the two ethoxylates at a total of 4% [8.5% of pigmented weight] yields a fluid suspension of pigments that remains homogeneous for at least 24 hours. Applying the liquid to the skin and allowing to dry yields a uniform, matte film.

EXAMPLE IB

Repeating Example I, but with the two ethoxylates at a total of about 9% [19% of pigment weight] allows the pigments to be dispersed to form a thin, homogeneous suspension that may be uniformly applied to the skin to form a matte film.

EXAMPLE II

[58.5% pigments by weight]

|   |   |   |
|---|---|---|
| (A) | water | 34.5 |
|  | potassium salt of phosphated N, N— bis ethoxylated coco amine oxide (crypto-anionic ethoxylate) | 2.5 |
|  | polysorbate 20 | 4.5 |
| (B) | titanium dioxide | 20.0 |
|  | kaolin | 15.0 |
|  | talcum | 20.0 |
|  | iron oxide powder, brown | 3.5 |

Procedure: Blend and mix (A) for 1 minute. Blend and mix (B) for 2 minutes. Mix (A) rapidly to create moderate vortex and slowly add (B). Mix rapidly to form a uniformly thick liquid. EXAMPLE III

[40% pigments by weight]

|   |   |   |
|---|---|---|
| (A) | water | 54.2 |
|  | acetylated polyoxyethylene (10) lanolin alcohol | 2.2 |
|  | polyoxyethylene glyceryl monolaurate | 3.6 |
| (B) | mica (and) bismuth oxychloride | 20.0 |
|  | mica (and) iron oxides (and) titanium dioxide | 10.0 |
|  | talcum | 10.0 |

Procedure: Blend and mix (A) for 1 minute. Blend and mix (B) for 2 minutes. Mix (A) rapidly to create moderate vortex and slowly add (B). Mix rapidly to form a uniformly thick liquid.

The following example includes additional excipients.

EXAMPLE IV

[51% pigments by weight]

|   |   |   |
|---|---|---|
| (A) | water | 33.8 |
|  | acrylic/acrylate copolymer (40% in ammonia water) | 5.0 |
|  | disodium edetate | 0.1 |
|  | propylene glycol | 3.0 |
|  | imidazolidinyl urea | 0.3 |
|  | methyl paraben | 0.2 |
| (B) | PEG-7 glyceryl cocoate | 1.6 |
|  | PEG-40 castor oil | 3.8 |
|  | fragrance | 0.1 |
| (C) | talc | 16.0 |
|  | titanium dioxide | 26.0 |
|  | attapulgite | 5.0 |
|  | iron oxide powder, brown | 5.0 |
|  | quaternium-15 | 0.1 |

Procedure: Blend and mix (A) for one minute. Blend and mix (B) for one minute. While mixing (A), add (B) and mix rapidly to create moderate vortex. Add (C). Mix rapidly to form homogenous, thick pourable liquid.

The present invention also may be utilized to prepare highly pigmented, cosmetically elegant liquid emulsions. Example V is one such emulsion.

EXAMPLE V

[41.6% pigments by weight]

|   |   |   |
|---|---|---|
| (A) | caprylic/capric triglyceride | 6.5 |
|  | mineral oil (and) lanolin alcohols | 2.9 |
|  | acetylated polyoxyethylene (10) lanolin alcohol | 2.0 |
|  | polyoxyethylene (20) sorbitan monolaurate | 1.0 |
|  | cetyl alcohol | 0.4 |
|  | propylene glycol stearate | 4.1 |
| (B) | titanium dioxide | 20.0 |
|  | talcum | 14.8 |
|  | kaolin | 4.0 |
|  | iron oxide powder, brown | 2.8 |
| (C) | water | 34.35 |
|  | glycerin | 2.5 |
|  | polyquaternium-10 | 0.4 |
|  | propylene glycol | 3.5 |
|  | hydroxyethylcellulose | 0.25 |
|  | methyl paraben | 0.2 |
|  | imidazolidinyl urea | 0.3 |

Procedure: Mix and heat (A) to 70° C. Mix and heat (C) to 70° C. While mixing (A), add (C). Mix rapidly to create vortex. Blend (B) and add to vortex. Mix and cool to 24°–28° C.

The preceding Example V may be prepared as a total block light screen (ultraviolet and visible light screen) by incorporating adequate levels of any oil-soluble and/or water-soluble ultraviolet absorbers (singly or in combination). Exemplary UV absorbers are listed by the OTC advisory panel to the U.S. Food and Drug Administration in Category I or are directly approved by the F.D.A. (or foreign government equivalent agency). The combination of adequate levels of chemical ultraviolet absorbers plus the physical protection afforded by high concentrations of Category I titanium dioxide as described in the examples of the present invention, yields a topical light screen of unprecedented protection in a cosmetically acceptable form.

A sunscreen prepared from Example V is as follows:

EXAMPLE VI

[31.5% pigments by weight]

|   |   |   |
|---|---|---|
| (A) | caprylic/capric triglyceride | 6.0 |

| | | |
|---|---|---|
| | -continued | |
| | mineral oil (and) lanolin alcohols | 2.9 |
| | acetylated polyoxyethylene (10) lanolin alcohol | 2.0 |
| | polyoxyethylene (20) sorbitan monolaurate | 1.0 |
| | cetyl alcohol | 0.5 |
| | octyl methoxycinnamate | 4.0 |
| (B) | titanium dioxide | 14.0 |
| | talcum | 14.0 |
| | kaolin | 4.0 |
| | iron oxide powder, brown | 2.5 |
| (C) | water | 36.0 |
| | glycerin | 3.0 |
| | propylene glycol | 3.0 |
| | polyquaternium-10 | 0.4 |
| | hydroxyethylcellulose | 0.2 |
| | methyl paraben | 0.1 |
| | imidazolidinyl urea | 0.3 |
| | quaternium-15 | 0.1 |
| | hydrolyzed animal protein | 1.0 |
| | benzophenone-4 | 5.0 |

Procedure: Mix and heat (A) to 70° C. Mix and heat (C) to 70° C. While mixing (A), add (C). Mix rapidly to create vortex. Blend (B) and add to vortex. Mix and cool to 24°-28° C.

A semi-solid (gel-like) suspension according to the the present invention may be readily prepared utilizing conventional thickening agents. Example VII demonstrates one such thickened composition:

EXAMPLE VII

[48.0% pigments by weight]

| | | |
|---|---|---|
| (A) | water | 43.43 |
| | carbomer 940 | 0.99 |
| (B) | trolamine 99% | 1.58 |
| (C) | polyoxyethylene (10) oleyl ether | 2.2 |
| | poloxamer 124 | 3.8 |
| (D) | titanium dioxide | 20.0 |
| | zinc oxide | 12.0 |
| | talcum | 12.0 |
| | iron oxide powder, brown | 4.0 |

Procedure: Blend (A) rapidly for 30 minutes. Then mix at moderate speed and add (B). Mix for 10 minutes. Add (C) and mix for 10 minutes. Blend and mix (D) for 2 minutes then, while mixing gel, sprinkle in D. Mix until uniform.

Example VII yields a semi-solid, cosmetically elegant, highly pigmented product that spreads and dries uniformly on the skin. A semi-solid (cream-like) emulsion according to the present invention may be readily prepared, for example, by increasing the concentration of waxy alcohol and ester in Example V, as shown in Example VIII below.

EXAMPLE VIII

[38.8% pigments by weight]

| | | |
|---|---|---|
| (A) | caprylic/capric triglyceride | 5.5 |
| | mineral oil (and) lanolin alcohols | 2.9 |
| | acetylated polyoxyethylene (10) lanolin alcohol | 2.0 |
| | polyoxyethylene (20) sorbitan monolaurate | 1.0 |
| | cetyl alcohol | 2.4 |
| | propylene glycol stearate | 8.6 |
| (B) | titanium dioxide | 20.0 |
| | talcum | 12.0 |
| | kaolin | 4.0 |
| | iron oxide powder, brown | 2.8 |
| (C) | water | 31.65 |
| | glycerin | 2.5 |
| | propylene glycol | 3.5 |
| | polyquaternium-10 | 0.4 |
| | hydroxyethylcellulose | 0.25 |
| | methyl paraben | 0.2 |
| | imidazolidinyl urea | 0.3 |

Procedure: Mix and heat (A) to 70° C. Mix and heat (C) to 70° C. While mixing (A), add (C). Mix rapidly to create vorte. Blend (B) and add to vortex. Mix and cool to 24°-28° C.

The cream-like semi-solid emulsion contains nearly 50% pigments, but spreads readily on the skin to give a cosmetically acceptable cover-up film.

The following comparative examples demonstrate the need for dual alkoxylated surfactants in order to achieve the desired cosmetic composition.

A. COMPARATIVE EXAMPLES

Use of one class of ethoxylated surfactant vs. two surfactants:

1.

(a) Repeating Example I (Total ethoxylates=6.0%), but utilizing only polyoxyethylene (10) oleyl ether at 2.2% results in a stiff non-mixable heavy paste.

(b) Repeating Example I with only polyoxyethylene (10) oleyl ether, at 6.0%, results in a flowable system with white streaks rapidly forming at the surface of the mixture. Remixing temporarily eliminates the white surface streaks which reappear within 10 minutes after mixing.

(c) Repeating Example I but only with polyoxyethylene (10) oleyl ether, at a midrange concentration of 4.1% yields a pasty, mixable mass that does not flow. Whitish dots appear on surface of mix one hour after preparation.

2.

(a) Repeating Example I, but utilizing only poloxamer 124 at 3.8% yields an unctuous paste. Separation of orange colored liquid appears at surface of product within 2 hours. Remixing yields same results.

(b) Repeating Example I, but utilizing only poloxamer 124 at 6.0% results in a mixture that allows for substantial settling of pigments out of suspension with clear, slightly orange fluid above pigments. Remixed and applied to skin surface, material dries in varied color streaks.

B. COMPARATIVE EXAMPLES

Replacement of non-ionic ethoxylate, polysorbate 20 by crypto-anionic ethoxylate in Example II:

1. Repeating Example II (total combined surfactants 7%), but utilizing only potassium salt of phosphated N,N-bis ethoxylated coco amine oxide at 7% of total formula results in a frothy non-uniform mixture with pigments rapidly settling out of suspension.

2. Repeating Example II but replacing polysorbate 20 (ethoxylated non-ionic) with the crypto-anionic surfactant pareth-25-7 carboxylic acid yields an unacceptable mixture similar in appearance to the preparation of Experiment B(1).

C. COMPARATIVE EXAMPLES

Replacement of non-ionic surfactant acetylated polyoxyethylene (10) lanolin alcohol in Example III with conventional anionic surfactant:
1. Repeating Example III (total combined surfactants, (5.8%), but replacing acetylated polyoxyethylene (10) lanolin alcohol with sodium lauryl sulfate (2.6% of total system) results in a frothy, whip cream-like mass that non-uniformly streaks the skin.

D. COMPARATIVE EXAMPLES

The limits on the amounts of surfactants relative to the amount of pigment included in the compositions according to this invention are shown by the following examples.
1. Repeating Example I, but with the two ethoxylates at a total of only 3.36 wt% [7% of pigment weight] results in a thick, paste-like mass.
2. Repeating Example I, but with the two ethoxylates at a total of 9.84% of total system [20.5% of pigment weight] gives a watery-thin dispersion of pigments that rapidly settle out of suspension.

I claim:
1. An aqueous cosmetic coverup composition comprising:
    about 23 to about 62 wt percent of a cosmetically acceptable water insoluble pigment;
    about 0.5 to about 6.5 wt percent of a first alkoxylated surfactant having an average number of alkoxy monomer units of about 3 to about 40 and selected from the group consisting of a polyethoxylated ether of a fatty acid alcohol; a polyethoxylated ether derivative of lanolin or the partial fatty acid ester thereof; a polyethoxylated ether derivative of sorbitol or the partial fatty acid ester thereof; or a polyethoxylated ether derivative of glycerol or partial fatty acid ester thereof;
    about 0.5 to about 6.5 wt percent of a second alkoxylated surfactant having an average number of alkoxy monomer units of about 3 to about 40 and selected from the group consisting of a polyethoxylated fatty acid; a polypropoxy/polyethoxy copolymer; an acetylated derivative of said first alkoxylated surfactant; or a phosphated polyethoxylated fatty acid amine oxide or salt thereof;
    about 30 to about 70 wt percent of H$_2$O;
    wherein the total amount of surfactants is about 2 to about 11.5 percent of the total composition weight and about 8.5 to about 19 percent of the pigment weight.
2. An aqueous coverup composition according to claim 1 wherein:
    said pigment is present in an amount of about 30 to about 60 wt percent of the total composition weight; and
    said first and said second alkoxylated surfactants are present in an amount of about 3 to about 9 wt percent based on the total composition weight.
3. A cosmetic composition according to claim 1 including an ultraviolet ray absorber having an absorbance bandwidth from about 0.2 microns to about 30 microns.
4. An aqueous cosmetic coverup composition, comprising:
    about 23 to about 62 wt percent of a cosmetically acceptable water insoluble pigment;
    about 0.5 to about 6.5 wt percent of a first alkoxylated surfactant;
    about 0.5 to about 6.5 wt percent of a second alkoxylated surfactant;
    about 30 to about 70 wt percent of H$_2$O;
    wherein the total amount of surfactants is about 2 to about 11.5 percent of the total composition weight and about 8.5 to about 19 percent of the pigment weight;
    and wherein said first and said second alkoxylated surfactant are of the formula

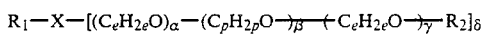

wherein:
R$_1$ is H; an alkyl or alkenyl radical derived from a fatty acid or mixture of fatty acids; a glyceryl, lanolin, or a sorbital radical derived from the removal of one hydroxyl group thereof; a fatty acid ester derivative of glyceryl, lanolin, or sorbital radical derived from the removal of one hydroxyl group of glyceryl, lanolin, or sorbitol respectively; an alkyl phenyl radical; or R$_3$;
R$_2$ is H, MSO$_4$, —SO$_3$H, M$_2$PO$_4$,

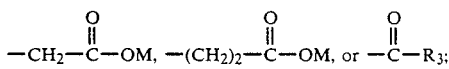

R$_3$ is a straight chain alkyl group having about 1 to about 22 carbon atoms;
X is —O—,

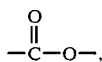

N, NH, N O,

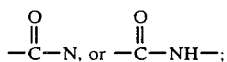

M is H or an alkali metal or ammonium cation;
e is 2 or 3;
p is 2 or 3;
e is not equal to p;
α is 1 to 40;
β is 0 to 40;
γ is 0 to 40;
δ is 1 or 2;
provided that when δ is 1, α is 3 to 40;
provided that when X is N, N O or

δ is 2 and α is 1 to 40;
further provided that if R$_2$ is MSO$_4$, SO$_3$H,

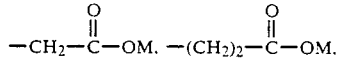

or M$_2$PO$_4$ for said first surfactant, then R$_2$ is H or

for said second surfactant;
further provided that if β is greater than zero for said first surfactant, then β and γ are both equal to zero for said second surfactant;
further provided that if β is not zero for both surfactants, then at least one of X or $R_1$ is different for said first and said second surfactants.

5. A cosmetic coverup composition according to claim 4 wherein:
said first surfactant is described by the formula of claim 4, when e is 2; and β and γ are 0; X is 0; $R_1$ is an alkyl or alkenyl radical derived from a fatty acid; and
said second surfactant is described by the formula of claim 4, when β is greater than zero; X is 0; $R_1$ and $R_2$ are H.

6. A cosmetic coverup composition according to claim 4 wherein:
said first surfactant is of the formula $R_1X-(C_2H_4O)_a-R_2$ where:
α is 3 to 40;
$R_1X$ is lanolin alkoxy;
$R_2$ is H, $MSO_4$, $M_2PO_4$, $SO_3H$ or

and where:
said second surfactant is of the formula $R_5X-(C_2H_4O)_a-R_4$

α is 3 to 40;
$R_5X$ is sorbitol or a partial fatty acid ester derivative of sorbitol;
$R_4$ is H, $MSO_4$, $M_2PO_4$, $SO_3H$ or

$R_3$ is a straight chain alkyl group having about 1 to about 22 carbon atoms;
provided that if $R_2$ is $MSO_4$, $SO_3H$, or $M_2PO_4$, then $R_4$ is H or

7. A cosmetic coverup composition according to claim 4 where:
said first surfactant is of the formula described in claim 4, where:
e is 2;
β and γ are 0;
δ is 1;
$R_1X$ is lanolin alkoxy;
and said second surfactant is of the formula described in claim 4, where:

e is 2;
β and γ are 0;
δ is 1;
$R_1X$ is glycerol or a partial fatty acid ester derivative of glycerol;
provided that if $R_2$ is $MSO_4$, $-SO_3H$ or $M_2PO_4$ for either of said first surfactants, then $R_2$ is H or

for the other said surfactant.

8. A cosmetic coverup composition according to claim 4 wherein:
said first surfactant is described according to the formula of claim 4, where
e is 2;
β and γ are 0;
δ is 1;
$R_1X$ is glycerol or a partial fatty acid ester derivative glycerol; and
said second surfactant is described according to the formula of claim 4, where:
e is 2;
β and γ are 0;
$R_1X$ is a fatty acid carboxy or a mixture of fatty acid carboxys, a fatty acid alkoxy or a mixture of fatty acid alkoxys, or a mixture of fatty acid, carboxys and fatty acid alkoxys;
provided that if $R_2$ is $MSO_4$, $SO_3H$ or $M_2PO_4$ for either of said surfactants, then $R_2$ is H or

said other surfactant.

9. A cosmetic coverup composition according to claim 4 wherein:
said first surfactant is described by the formula of claim 4, where:
e is 2;
β and γ are 0;
δ is 2;
X is N, N→O or

$R_1$ is one or more alkyl or alkenyl radicals derived from a fatty acid or a mixture of fatty acids;
$R_2$ is $MSO_4$, $-SO_3H$ or $M_2PO_4$; and wherein:
said second surfactant is described by the formula of claim 4, where:
e is 2;
β and γ are 0;
δ is 1;
$R_1X$ is sorbitol or a partial fatty acid ester of sorbital; and
$R_2$ is H or

10. An aqueous cosmetic coverup composition which is flowable, spreadable, nonstreaking and greaseless, comprising:

about 30 to about 60 wt percent of a cosmetically acceptable water insoluble pigment;

about 1 to about 6 wt percent of a first alkoxylated surfactant selected from the group consisting of polyoxyethylene (10) oleyl ether, PEG-7 glyceryl cocoate, acetylated polyoxyethylene (10) lanolin alcohol, and an alkali salt of phosphated N,N-bis ethoxylated coco amine oxide;

about 1 to about 6 wt percent of a second alkoxylated surfactant selected from the group consisting of poloxamer 124, polysorbate 20, polyoxyethylene glyceryl monolaurate having an average number of ethoxy monomer units of about 3 to about 40, PEG-40 castor oil, and polyoxyethylene (20) sorbitan monolaurate;

about 30 to about 70 wt percent of $H_2O$; wherein the total amount of surfactant is about 3 to about 11 wt percent of the total composition and about 8.5 to about 19 percent of the pigment wt.

11. A cosmetic coverup composition according to claim 10, wherein:

said first surfactant is polyoxyethylene (10) oleyl ether; and said second surfactant is poloxamer 124.

12. A cosmetic coverup composition according to claim 11 wherein:

said first surfactant is the potassium salt of phosphated N,N-bis ethoxylated coco amine oxide; and said second surfactant is polysorbate 20.

13. A cosmetic coverup composition according to claim 11 wherein:

said first surfactant is acetylated polyoxyethylene (10) lanolin alcohol; and said second surfactant is polyoxyethylene glyceryl monolaurate.

14. A cosmetic coverup composition according to claim 11 wherein:

said first surfactant is PEG-7 glycerylcocoate; and said second surfactant is polyoxyethylene glyceryl monolaurate.

15. A composition according to claim 11 wherein:

said first surfactant is acetylated polyoxyethylene (10) lanolin alcohol;

said second surfactant is polyoxyethylene (20) sorbitan monolaurate.

* * * * *